United States Patent [19]

Seely et al.

[11] Patent Number: 5,079,145
[45] Date of Patent: Jan. 7, 1992

[54] PROCESS FOR PREPARING MICROORGANISMS USED FOR MAKING PHENYL ACETYL CARLINOL (PAC)

[75] Inventors: Robert J. Seely, Loveland; Donald L. Heefner, Boulder; Robert V. Hageman, Boulder; Michael J. Yarus, Boulder; Sally A. Sullivan, Boulder, all of Colo.

[73] Assignee: Synergen Associates, Inc., Boulder, Colo.

[21] Appl. No.: 261,010

[22] Filed: Oct. 21, 1988

[51] Int. Cl.$^5$ .......................... C12Q 1/04; C12P 7/26; C12P 7/22; C12N 1/38

[52] U.S. Cl. ...................... 435/34; 435/148; 435/156; 435/172.1; 435/173; 435/244; 435/245; 435/254; 435/255; 435/921; 435/942

[58] Field of Search ............... 435/148, 244, 245, 255, 435/34, 156, 172.1, 254, 173, 921, 942

[56] References Cited

U.S. PATENT DOCUMENTS

| | | | |
|---|---|---|---|
| 215,287 | 10/1878 | Pennington | 435/34 |
| 3,338,796 | 8/1967 | Rothrock | |
| 3,919,052 | 11/1975 | Fresnel et al. | |
| 4,140,580 | 2/1979 | Gibson et al. | 435/34 |
| 4,235,964 | 11/1980 | Bochner | 435/34 |
| 4,299,915 | 11/1981 | Thilly et al. | 435/34 |
| 4,675,288 | 6/1987 | Falck | 435/34 |
| 4,732,852 | 3/1988 | Wood et al. | |

FOREIGN PATENT DOCUMENTS 1280281 12/1986 Japan ................................. 435/34

OTHER PUBLICATIONS

Voets, J. P., et al., Phenylacetylcarbinol biosynthesis by Saccharomyces cerevisiae, Z. Allg. Mikrobiol. 1973, 13(4), 355-65 (1973), as reported in Chemical Abstracts 76 CA 40882b.

Gupta, K. G. et al., Production of phenyl acetyl carbinol by yeasts, Biotechnol. Bioeng. 21(b), 1085-9 (1979), as reported in Chemical Abstracts 91 CA 35391j.

Netrval, J. et al., Production of phenyl acetyl carbinol and ephedrine-less known area of yeast utilization in industry, Kvasny Prum. 28(b), 131-4 (1982), as reported in Chemical Abstracts 97 CA 161037K.

Ellaiah, P. et al., Studies on the production of phenyl acetly carbionol from benzaldehyde by Saccharomyces cerevisiae, Indian Drugs 24(4), 192-5 (1987), as reported in Chemical Abstracts 106 CA 192466h.

Agarwal, S. C. et al., Studies on the production of L-acetylphenylcarbinol by yeast employing benzaldehyde as precursor, Biotechnol. Bioeng. 29(b), 783-5 (1987), as reported in Chemical Abstracts 106 CA 194721m.

Tripathi, C. K. M. et al., Continuous cultivation of a yeast strain and biotransformation of L-acetyl phenyl carbionol (L-PAC) from benzaldehyde, Biotechnol. LeH. 10(9), 635-b (1988), as reported in Chemical Abstracts 109 CA 228674c.

Bringer-Meyer, S. et al., Acetoin and phenylacetylcarbinol formation by pyruvate decarboxylases of Zymomonas mobilis and Saccharomyces carlsbergensis, Biocatalysis 1(4), (1988), as reported in Chemical Abstracts 110 CA 20374t.

Long, A. et al., Biotransformation of aromatic aldehydes by Saccharomyces cerevisiae: investigation of reaction rates, J. Ind. Microbiol. 4(1), 49-53 (1989), as reported in Chemical Abstracts 110 CA 113139k.

Ellaiah, P. et al., Effect of aeration and alternationg current on the production of phenyl acetyl carbinol by Saccharomyces cerevisiae, Indian J. Technol. 26(10), 509-10 (1988), as reported in Chemical Abstracts 110 CA 133635x.

Primary Examiner—Herbert J. Lilling
Attorney, Agent, or Firm—Finnegan, Henderson, Farabow, Garrett & Dunner

[57] ABSTRACT

Mutations are induced in a microorganism selected from the species *Saccharomyces cerevisiae* or from the species *Candia flareri*. The resulting mutants are cultured in the presence of a fermentation inhibitor, such as acetaldehyde, ephedrine or PAC-dione, to form colonies having resistance to the inhibitor. Cells from the colonies are isolated and tested for yield of phenyl acetyl carbinol (PAC) in a fermentation with benzaldehyde and pyruvate. Yeast cells from the colonies that produce elevated levels of PAC are selected for use in subsequent fermentations. PAC is useful as an intermediate in the preparation of 1-ephedrine and d-pseudoephedrine, two well-known medicinal chemicals.

6 Claims, 5 Drawing Sheets

PROCESS FOR PREPARING MICROORGANISMS USED FOR MAKING PHENYL ACETYL CARLINOL (PAC)

BACKGROUND OF THE INVENTION

This invention relates to a method of making phenyl acetyl carbinol (PAC), which is useful as an intermediate in the manufacture of l-ephedrine and d-pseudoephedrine. This invention also relates to microorganisms especially adapted for use in the manufacture of phenyl acetyl carbinol and to a method for providing the microorganisms.

Pseudoephedrine and ephedrine are two major medicinal chemicals. Pseudoephedrine is useful as a nasal decongestant and is found as an ingredient in cough and cold capsules, sinus medications, nose sprays, nose drops and allergy and hay fever medications. Ephedrine is useful as a topical nasal decongestant, a treatment for mild forms of shock (CNS stimulant) and as a bronchodilator.

L-ephedrine is a natural product found in various species of plants. L-ephedrine is obtained from dried plant material by an initial treatment with alkali followed by extraction with organic solvent. While d-pseudoephedrine is also found in nature, it is more easily obtained in high yield from l-ephedrine by Welsh rearrangement.

L-phenyl acetyl carbinol (PAC) is the key intermediate in the synthesis of l-ephedrine. The transformation of benzaldehyde to L-(−)phenyl acetyl carbinol by Brewer's yeast was first described by Newberg and Hirsch. *Biochem. Z.*, 115:282–310 (1921). More particularly, benzaldehyde can be transformed by a fermenting yeast into L-(−) phenyl acetyl carbinol as follows:

(−) PAC

The combination of yeast transformation of benzaldehyde to produce PAC and chemical conversion of the PAC to make l-ephedrine is described in U.S. Pat. No. 1,956,950. The PAC can be converted by a chemical reductive amination with methylamine to optically pure L-ephedrine as follows:

(−) PAC      (−) EPHEDRINE (R,S)

The l-ephedrine can then converted in high yield to d-pseudoephedrine as follows:

(−) EPHEDRINE (R,S)

(+) PSEUDOEPHEDRINE (S,S)

It is apparent from this reaction scheme that microbial transformation of benzaldehyde by yeast to form L-(−)phenyl acetyl carbinol in high yield and purity is of prime importance for successful commercial operation of the synthetic route.

Prior processes for the production of PAC from yeast involve the addition of the yeast to a medium containing molasses, beer wort, $MgSO_4$ and other salts at a pH of 5.5–6.0. After an initial short period of stirring and aeration, a mixture of acetaldehyde and benzaldehyde is added in portions. A final concentration of PAC of about 7.5 g/L is obtained in 5–10 hours of continued stirring and aeration. With brewer's or baker's yeast, benzyl alcohol is always observed as a co-product. The highest reported yield of PAC based on benzaldehyde is about 73%. The remaining benzaldehyde is converted to the alcohol. Acetaldehyde is not essential for PAC production, but addition of this compound is required in order to achieve the highest yields of PAC.

Most of the literature concerning the synthesis of PAC by fermenting yeast deals with yield optimization. There is a general consensus that high levels of yeast are needed to obtain relatively low levels of PAC. The available literature suggests that the current yeast transformation of benzaldehyde to PAC is inefficient and yeast productivity is low. The yeast cannot be used for multiple batches because PAC production drops with increased exposure to the substrates and to the end product.

In addition, current yeast transformation provides only low concentrations of PAC in the fermentation liquor. This requires large process volumes and consequently large volumes of extraction solvent, which adversely impact on labor and utility costs in commercial operations.

In addition, the yield of PAC from benzaldehyde is decreased as a result of the catalytic reduction of benzaldehyde by an alcohol dehydrogenase to form benzyl alcohol, which is an unwanted by-product. All of the PAC-producing strains that have been examined produce benzyl alcohol.

Accordingly, there exists a need in the art for an improved method of making PAC by yeast transformation of benzaldehyde. The method should provide a higher yeast productivity and higher maximum concentrations of PAC in the fermentation liquor than heretofore possible. In addition, the catalytic reduction of benzaldehyde to benzyl alcohol should be minimized.

SUMMARY OF THE INVENTION

This invention aids in fulfilling these needs in the art by providing an improved process for the production of PAC by yeast transformation of benzaldehyde. The process of this invention makes it possible to obtain higher yeast productivity and higher concentrations of PAC in the fermentation liquor than in present processes.

More particularly, this invention provides a process for the production of L-phenyl acetyl carbinol (PAC) wherein the process comprises providing a submerged culture of a microorganism in an aqueous fermentation medium containing assimilable carbon. The organism is cultivated under anaerobic or oxygen-limited conditions in the presence of benzaldehyde and pyruvate to form PAC in a concentration of at least about 1.0 g/L in the fermentation medium. The organism is a mutant of a parent strain of *Saccharomyces cerevisiae* or a mutant of a parent strain of *Candida flareri*. The mutant is more resistant to aldehyde inhibition, produces less acetaldehyde and provides a higher concentration of PAC in the fermentation medium than a corresponding fermentation using the parent strain under otherwise identical conditions. The PAC can be separated from the fermentation medium.

This invention also provides a method for producing the mutant microorganisms. The method comprises providing a microorganism capable of producing a measurable amount of L-phenyl acetyl carbinol (PAC) when cultured with benzaldehyde and pyruvate in an aqueous medium, wherein the organism is selected from species of *Saccharomyces cerevisiae* or from species of *Candida flareri*. The organism is chemically mutagenized with a chemical mutagen or by irradiation. The resulting mutated organisms are cultured in the presence of acetaldehyde under conditions to form colonies having resistance to acetaldehyde. Yeast cells are isolated from the colonies and tested for yield of L-phenyl acetyl carbinol in a fermentation with benzaldehyde and pyruvate. Cells from colonies producing elevated levels of PAC can be employed in large scale fermentation.

This invention provides similar processes in which the mutated organisms are cultured in the presence of either ephedrine or PAC-dione under conditions to form colonies having resistance to these substances. Yeast cells are isolated and tested as previously described.

Finally, this invention provides biologically pure cultures of mutant organisms capable of producing elevated levels of PAC when cultured with benzaldehyde and pyruvate in an aqueous medium. The cultures are identified herein as *Saccharomyces cerevisiae* P2180-1A-8pa and *Candida flareri* dgr. The invention includes mutants and variants of these strains that are capable of producing elevated levels of PAC under the conditions previously described.

BRIEF DESCRIPTION OF THE DRAWINGS

This invention will be more fully understood by reference to the drawings in which.

DESCRIPTION OF THE PREFERRED EMBODIMENTS

The process of this invention is especially adapted to produce L-phenyl acetyl carbinol (PAC) in high yield by microbial transformation. The abbreviation "PAC" is used herein to refer to the stereospecific form of phenyl acetyl carbinol identified as L-(−)phenyl acetyl carbinol. The designation L-(−)phenyl acetyl carbinol is used interchangeably with the designation 1-phenyl acetyl carbinol, and both designations are abbreviated as "PAC".

PAC is prepared by the transformation of benzaldehyde and pyruvate. The expression "pyruvate" is used in its conventional sense as referring to the moiety.

The transformation of benzaldehyde and pyruvate is carried out in the process of this invention with a mutant strain of a microorganism. The term "mutant" as used herein is intended to include all progeny of a parent microorganism in which there is a difference in genotype between the parent strain and its progeny. The term is also intended to include progeny in which there is a phenotypic difference from the parent strain with or without a difference in genotype. Of course, the term additionally includes progeny that exhibit differences in both genotype and phenotype from the parent strain.

More particularly, the method of the invention is carried out with mutants of *Saccharomyces cerevisiae* and *Candida flareri*, which efficiently convert pyruvic acid and benzaldehyde to 1-phenyl acetyl carbinol. The species of yeast employed in the conversion are capable of producing the enzyme pyruvate decarboxylase and thus contain endogenous pyruvate decarboxylase. The abbreviation "PDCase" when used herein means the enzyme pyruvate decarboxylase.

Pyruvate decarboxylase catalyzes the conversion of benzaldehyde to PAC. This enzyme is also capable of converting the pyruvate to acetaldehyde. The formation of acetaldehyde is believed to inhibit the enzyme, which is the apparent cause of a decrease in the yield of PAC from benzaldehyde. This invention provides mutant strains with resistance to aldehyde inhibition. By this it is meant that, in comparison to the parent strain, there is a reduction in the inhibition of activity of the mutant strain in the conversion of benzaldehyde as evidenced by the concentration of PAC in the fermentation medium. The concentration of PAC in the fermentation medium is higher with the mutant strain than with the parent strain when two fermentations carried out under otherwise identical conditions are compared. In the preferred embodiments of this invention, the mutant strains also produce less acetaldehyde from the benzaldehyde than the parent strain.

Mutations are induced in a microorganism selected from the species *Saccharomyces cerevisiae* or species of *Candida flareri*. The resulting mutants are cultured in the presence of acetaldehyde under conditions to form colonies having resistance to acetaldehyde inhibition. Cells from the colonies are isolated and tested for yield of PAC in a fermentation with benzaldehyde and pyruvate. The cells can also be tested for yield of acetaldehyde. It is thus possible to select yeast cells from the colonies that produce PAC at elevated levels and produce acetaldehyde at reduced levels, and to use these organisms for the production of PAC with improved yields as compared to the parent strains. The production of PAC in higher yields in a commercial operation is especially advantageous since the cost of production will be reduced.

Methods of preparing the mutant yeast strains having induced mutations will be initially described. This will be followed by a description of conditions for cultivating and selecting the mutants for elevated levels of PAC production. A description of conditions for using the mutants in the transformation of benzaldehyde to PAC will then be provided.

1 Preparation of Microorganisms With Induced Mutations

A wild-type yeast can be mutagenized with a chemical mutagen, such as methylnitrosoguanidine, nitrous acid or ethylmethane sulfonate. A preferred chemical mutagen is N-methyl-N'-nitro-N-nitrosoguanidine (NTG). A wild-type yeast can also be mutagenized by irradiation with ultraviolet light or with ionizing radiation, such as gamma radiation.

2. Cultivation of Mutant Yeasts

Mutant strains resistant to acetaldehyde, pyruvic aldehyde, propionaldehyde, formaldehyde, furfural, glyoxal, and α-ketobutyric acid can be prepared. More particularly, active PAC-producing mutant strains can be obtained as follows.

Using the microorganisms having induced mutations prepared as described above, mutants resistant to acetaldehyde can be cultivated by placing plates spread with a mutant strain into jars containing a small amount of acetaldehyde. Because acetaldehyde is volatile, the atmosphere becomes saturated with acetaldehyde when the jars are closed. To insure that resistant mutants grow and form colonies under these conditions, whereas the parent strain does not, the acetaldehyde should be employed in an amount of about 350 ul to about 1000 ul. For example, about 350 ul of acetaldehyde can be added to a 3.75 l jar.

Using this procedure, mutations were induced in *S. cerevisiae* P 2180-1A, a wild-type (WT) haploid strain, using N-methly-N'-nitro-N-nitrosoguanidine. A number of mutants were selected for resistance to pyruvate aldehyde. The mutants are identified in Table 1.

TABLE 1

Mutants Obtained by Treatment of *S. cerevisiae* P-2180-1A With Methylnitrosoguanidine and Cultivated for Resistance to Acetaldehyde

| Strain |
| --- |
| P-2180-1A (WT) |
| P-2180-1A-1$_{pa}$ |
| P-2180-1A-2$_{pa}$ |
| P-2180-1A-3$_{pa}$ |
| P-2180-1A-4$_{pa}$ |
| P-2180-1A-5$_{pa}$ |
| P-2180-1A-6$_{pa}$ |
| P-2180-1A-7$_{pa}$ |
| P-2180-1A-8$_{pa}$ |
| P-2180-1A-9$_{pa}$ |
| P-2180-1A-10$_{pa}$ |
| P-2180-1A-11$_{pa}$ |
| P-2180-1A-12$_{pa}$ |
| P-2180-1A-13$_{pa}$ |
| P-2180-1A-14$_{pa}$ |
| P-2180-1A-15$_{pa}$ |
| P-2180-1A-16$_{pa}$ |
| P-2180-1A-17$_{pa}$ |
| P-2180-1A-23$_{pa}$ |
| P-2180-1A-25$_{pa}$ |

Strains resistant to other inhibitors can be cultivated using a similar technique. For example, strains can be cultivated in the presence of 2,3-dihydroxybenzaldehyde, 2,4-dihydroxybenzaldehyde, 2,5-dihydroxybenzaldehyde, 3,4-dihydroxybenzaldehyde, furfural (2-formaldehyde), glyoxal, formaldehyde, and propionaldehyde using similar procedures. If the aldehyde to be used is not volatile, the aldehyde is preferably incorporated into the medium rather than added to a sealed jar.

3. Selection and Screening of Aldehyde Resistant Mutant Strains for Production of PAC To assay effectiveness of each of the mutant yeast strains in producing PAC, batch fermentations can be performed as follows. A known amount of cells, either immobilized or free, are added to a buffer solution containing the requisite substrates. Specifically, a standard reaction mixture suitable for the production of PAC in batch mode consists essentially of the following components:

| | |
| --- | --- |
| Potassium Citrate buffer, pH 6.0 | 100 mM |
| Magnesium Chloride (MgCl$_2$) | 1 mM |
| Polyethylene Glycol-1000 (PEG-1000) | 20% |
| Sodium Pyruvate | 110 mM |
| Benzaldehyde (Technical grade) | 100 mM |

The standard reaction mixture containing the cells is then shaken at room temperature for several hours. Cell samples are taken at various time intervals and centrifuged. The resulting supernatant is quantitatively analyzed for the presence of PAC. The PAC assay was modified from Eggleton et al., Biochem. J. 37:526:–529 (1943). Specifically, the procedure of Eggleton et al. is for the quantitation of diacetyl compounds by adsorption at 525 nm. PAC is assayed by its adsorption at 575 nm, and the adsorption reading is corrected for any contributions of 525 nm adsorbing species.

Each of the strains identified in Table 1 was examined for its ability to produce PAC as evidenced by the concentration of PAC in a culture medium after fermentation with benzaldehyde and pyruvate under the conditions described above. The concentration of PAC (mM)

in the fermentation medium after 5 hours is shown in Table 2 for each microorganism.

TABLE 2

PAC Production by *S. cervisiae* P-2180-1A and Mutants Thereof

| Number | [PAC, mM] |
|---|---|
| P-2180-1A (WT) | 33.8 |
| P-2180-1A-1$_{pa}$ | 24.5 |
| P-2180-1A-2$_{pa}$ | 37.0 |
| P-2180-1A-3$_{pa}$ | 35.8 |
| P-2180-1A-4$_{pa}$ | 36.2 |
| P-2180-1A-5$_{pa}$ | 30.3 |
| P-2180-1A-6$_{pa}$ | 37.9 |
| P-2180-1A-7$_{pa}$ | 36.6 |
| P-2180-1A-8$_{pa}$ | 51.8 |
| P-2180-1A-9$_{pa}$ | 37.0 |
| P-2180-1A-10$_{pa}$ | 35.3 |
| P-2180-1A-11$_{pa}$ | 57.5 |
| P-2180-1A-12$_{pa}$ | 51.4 |
| P-2180-1A-13$_{pa}$ | 36.8 |
| P-2180-1A-14$_{pa}$ | 35.2 |
| P-2180-1A-15$_{pa}$ | 27.5 |
| P-2180-1A-16$_{pa}$ | 56.1 |
| P-2180-1A-17$_{pa}$ | 26.4 |

The results reported in Table 2 show that the mutant strain *S. cerevisiae* P-2180-1A-8pa was substantially more effective in the production of PAC under the stated conditions than the wildtype (WT) strain P-2180-1A. The improved performance of this mutant is believed to be the result of a reduction in inhibition of PDCase by aldehyde.

Benzaldehyde/pyruvate fermentations using the parent strain *S. cerevisiae* P-2180-1A and several of its mutants were carried out, and the fermentation medium was sampled in each case after fermentation times 3 hours and 5 hours. The results are shown in FIG. 1.

Figure 1:
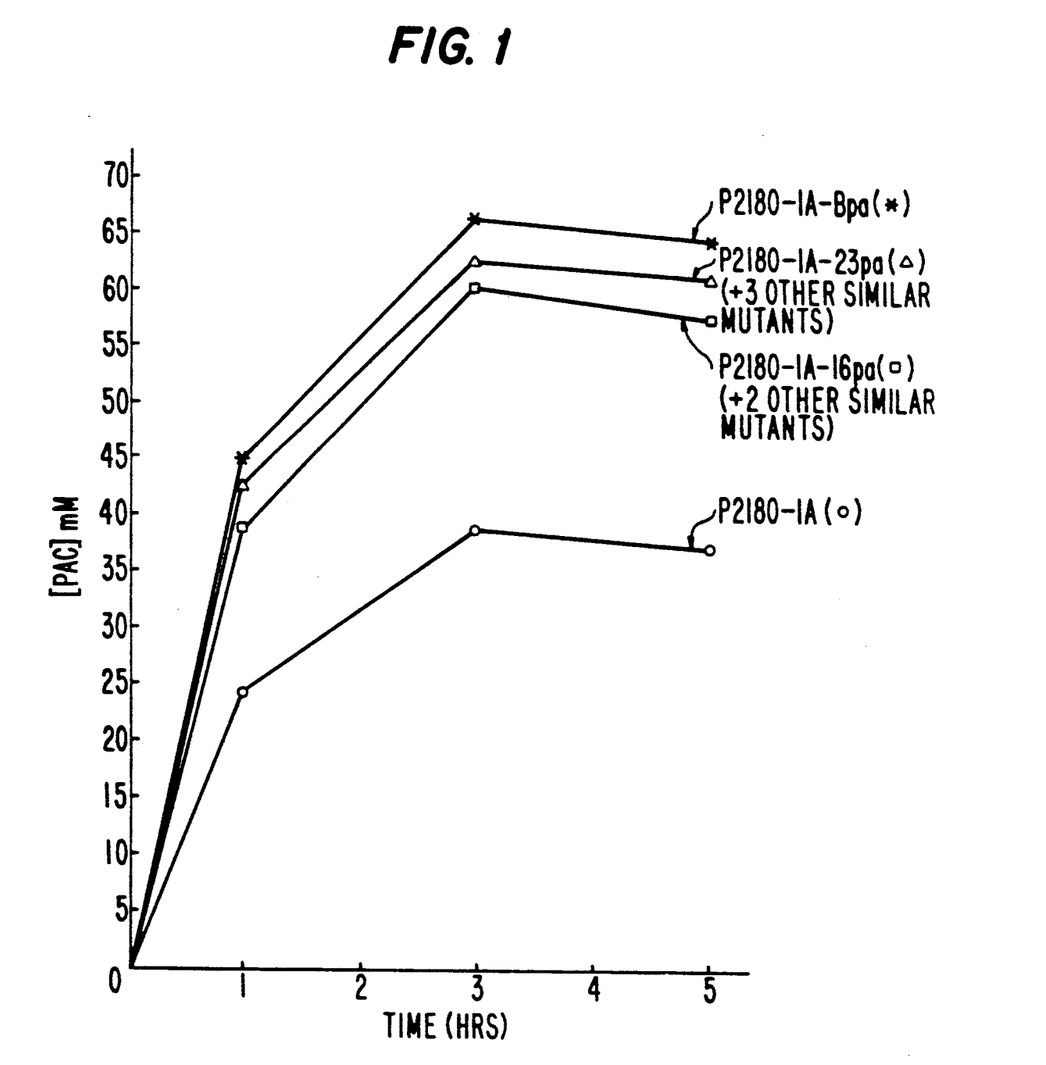
FIG. 1 is a graph showing the concentration of L-phenyl acetyl carbinol (PAC) as a function of time in a benzaldehyde/pyruvate fermentation using a parent strain of *S. cerevisiae* and several mutant strains thereof.

Referring to FIG. 1, all of the strains exhibited similar patterns of fermentation kinetics insofar as the rate of formation of PAC was initially very rapid. This was followed by a slower rate of PAC formation, and finally, there was a slight decline in PAC concentration due to the instability of PAC in the fermentation medium. It is evident from FIG. 1 that mutant strain P-2180-1A 8pa gave the highest yield of PAC at each of the fermentation times at which measurements were made. This mutant was substantially superior to its parent strain P-2180-1A in the yield of PAC. Mutant strain P-2180-1A-23pa and mutant strain P-2180-1A-16pa were also superior to the parent strain P-2180-1A in the yield of PAC.

Figure 2:
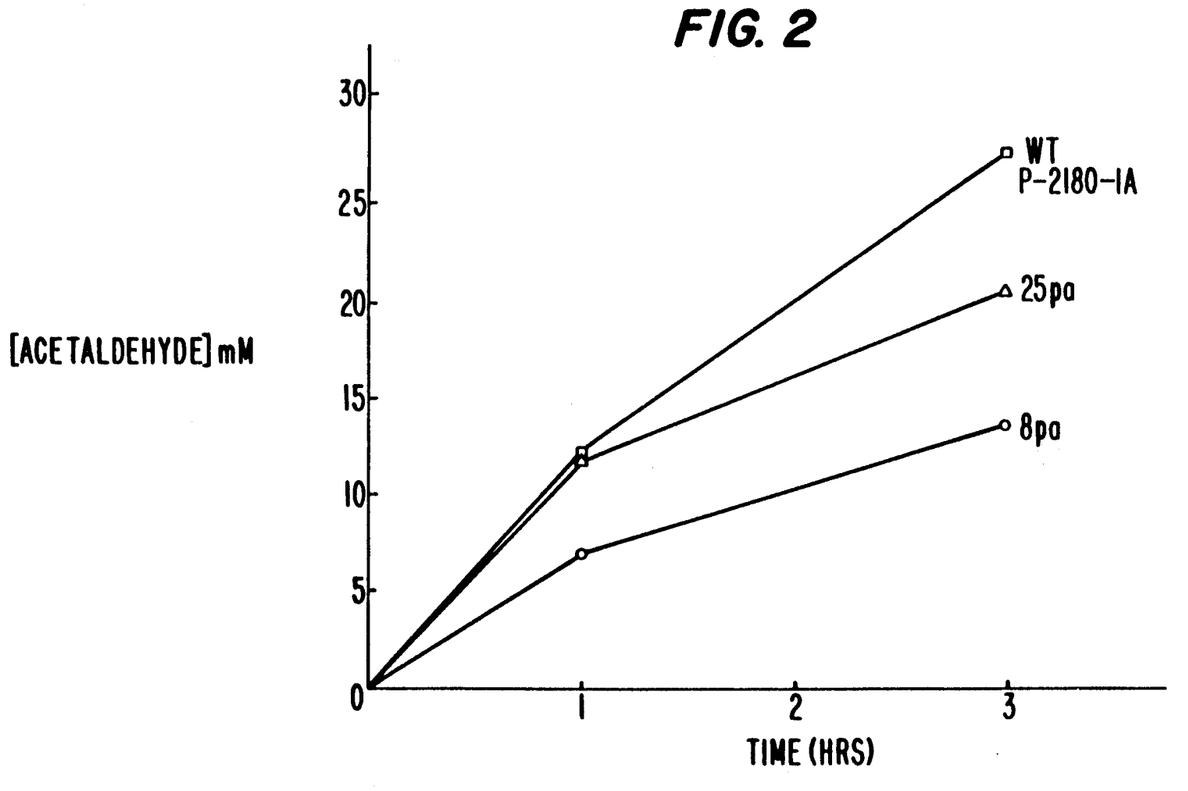
FIG. 2 is a graph showing acetaldehyde concentration as a function of time in a benzaldehyde/pyruvate fermentation using a parent strain of *S. cerevisiae* and several mutant strains thereof.

In addition, the mutant *S. cerevisiae* P-2180-1A-8pa produces significantly less acetaldehyde than its parent strain in a benzaldehyde/pyruvate fermentation. Specifically, FIG. 2 shows the concentration of acetaldehyde (mM) in the fermentation medium. The acetaldehyde concentration was greater for the parent strain P-2180-1A than for the mutant strain P-2180-1A-8pa at each of the reaction times at which the medium was sampled. The reduction in acetaldehyde concentration may be a causative factor in the observed elevation of PAC production by the mutant strain P-2180-1A-8pa. Mutant *S. cerevisiae* P-2180-1A-25pa also produced less acetaldehyde than the parent strain as is evident from FIG. 2.

Mutant strain P-2180-1A-8pa has another characteristic which distinguishes it from its parent. It is well known that pyruvate is a poor substrate for growth for *S. cerevisiae*. The mutant grows much better with pyruvate as a carbon source than does the parent strain. That the mutant P-2180-1A-8pa grows well on pyruvate and the parent does not suggests that the conversion of pyruvate to acetaldehyde is responsible for growth inhibition. The mutant apparently escapes the inhibitory effect of acetaldehyde because it was selected for its aldehyde resistance.

In order to demonstrate resistance to the inhibiting effect of 2,3-dihydroxybenzaldehyde on cell metabolism, *S. cerevisiae* P-2180-1A and the mutant P-2180-1A 8pa were each plated on growth media in culture dishes. The cultures were impregnated with equal amounts of the aldehyde. The resulting cell colonies were examined, and it was found that the mutant showed a much smaller zone of inhibition (clear area) than the parent strain. This indicated that *S. cerevisiae* P 2180-1A 8pa was much more resistant to the inhibitory effect of this aldehyde than its parent strain. Similar results were obtained for resistance of mutant P-2180-1A-8pa to formaldehyde, glyoxal, and 2-furaldehyde inhibition.

In addition to strain P-2180-1A-8pa, mutant strains of *S. cerevisiae* resistant to formaldehyde, 2,3-dihydroxybenzaldehyde and furfural were obtained. None was better at producing PAC than the parent strain P-2180-1A.

Mutants of *C. flareri* dgr resistant to acetaldehyde were also prepared as described above. None of these was superior to the parent strain at forming PAC from pyruvic acid and benzaldehyde.

In addition to selecting mutants resistant to aldehydes, two other approaches were used to either increase the amount of pyruvate decarboxylase in the cells or to alter the characteristics of the enzyme. The cultivation and selection procedures were the same as those used for aldehyde resistance, except that agar plates were used instead of jars.

Figure 3:
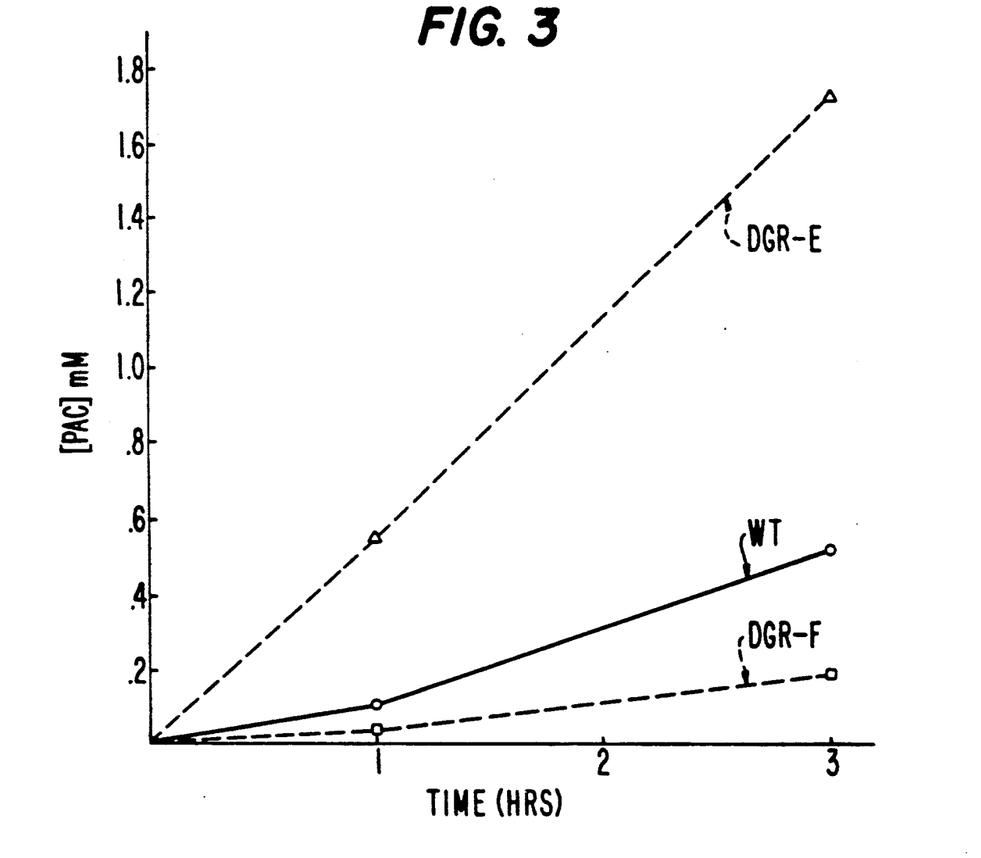
FIG. 3 is a graph showing concentration of PAC as a function of time for strains of *C. flareri*.

The first approach was to select mutants resistant to analogues of the product of the pyruvate-plus-benzaldehyde reaction. Mutants resistant to ephedrine were selected. From the experiment designed to select ephedrine-resistant strains of *C. flareri* dgr (a deoxyglucose-resistant derivative of *C. flareri*) mutants *C. flareri* dgr E, D, and G, were obtained. Each strain was assayed for PAC production using the procedure previously described. FIG. 3 shows the concentration of PAC (mM) obtained with the wild type strain (WT) and with two of the mutants. The mutant *C. flareri* dgr E (DGR-E) was found to be substantially superior to the WT strain in PAC production. Both the rate of PAC formation and the final concentration of PAC in the fermentation medium were superior with the mutant DGR-E. On the other hand, the mutant *C. flareri* dgr F (DGR-F) gave less favorable results than the WT strain. The results in FIG. 3 demonstrate the need for care in selecting suitable mutant strains.

Figure 4:
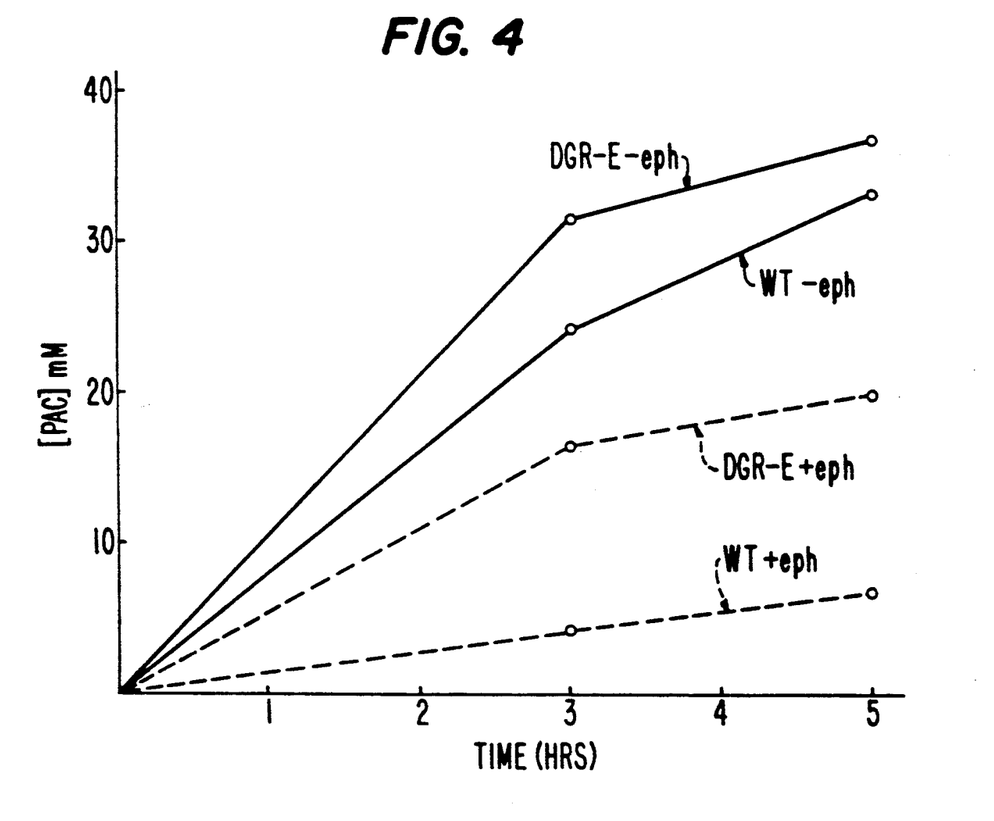
FIG. 4 is a graph comparing the effect of ephedrine on the rate and extent of PAC formation using strains of *C. flareri*.

The mutant DGR-E was further examined to determine whether ephedrine in the fermentation medium affected PAC production. It was found that both the rate and extent of PAC production were superior when mutant DGR-E was compared with the WT strain. The results are shown in FIG. 4. The presence of ephedrine (+eph) in the fermentation medium inhibited PAC formation with both the mutant DGR-E and the WT strains, but the mutant strain was less affected that the parent strain. The results in FIG. 4 also confirm the results in FIG. 3, namely, that mutant DGR-E is superior to the WT strain in PAC production in the absence of ephedrine (−eph) in the fermentation medium.

Figure 5:
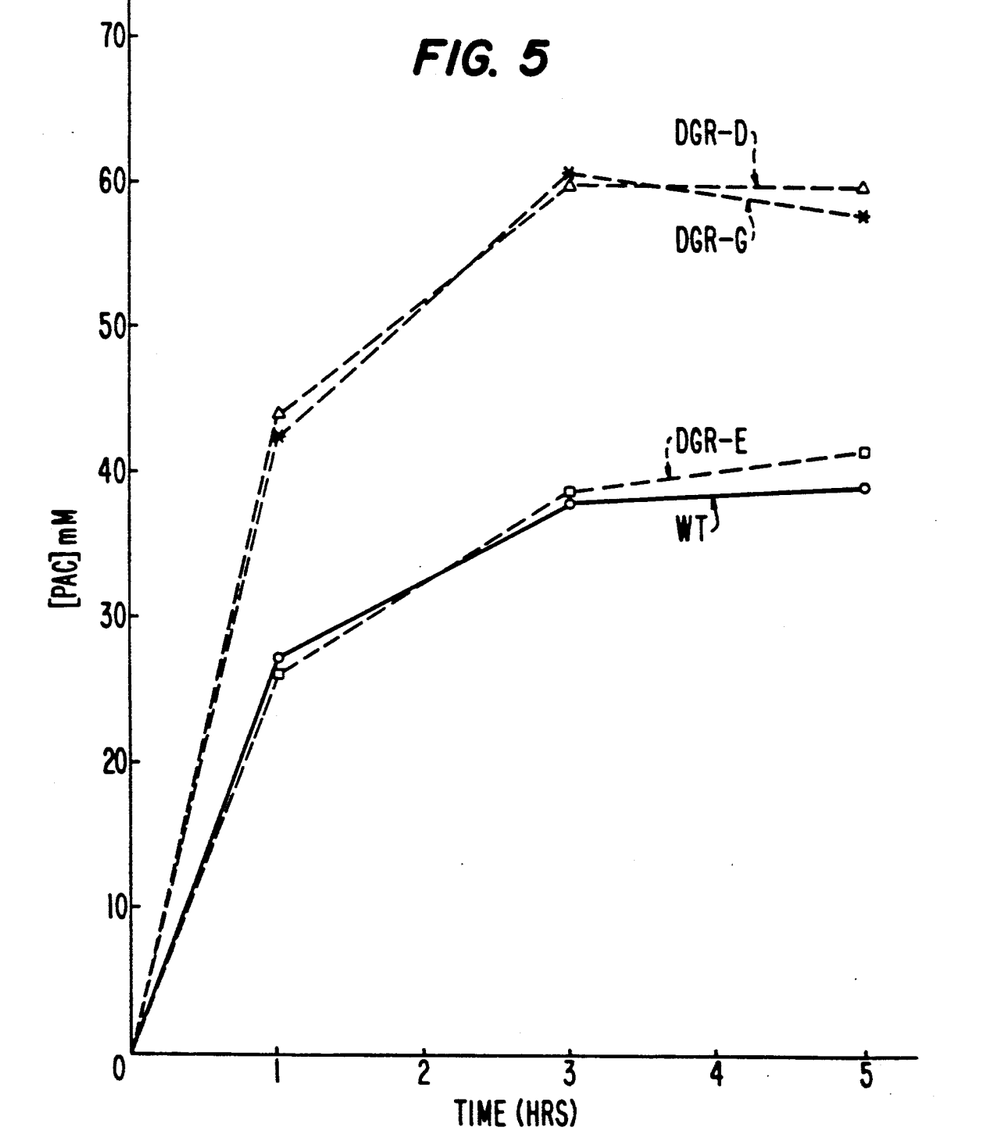
FIG. 5 is a graph comparing the rate and amount of PAC formation using a wild-type and three mutant strains of *C. flareri*.

FIG. 5 shows that two other isolates, namely dgr D and dgr G, are significantly superior to the parent in the absence of ephedrine.

Mutants of *S. cerevisiae* resistant to ephedrine yielded no superior PAC producers.

The second approach was to select mutants of *C. flareri* dgr for resistance to PAC-dione, another PAC analogue. PAC-dione has the formula:

Although PAC-dione resistant isolates produced more PAC in the presence of the dione than did the parent, none was superior in the absence of the dione.

Mutants of *S. cerevisiae* resistant to PAC-dione were also selected, and none of these was better than the parent strain at synthesizing PAC from pyruvate and benzaldehyde.

4. PAC Production by Microbial Transformation of Benzaldehyde and Pyruvate

The mutant strains prepared as described above can be used to prepare PAC in an aqueous fermentation medium. The process of the invention can be carried out in a conventional bioreactor. Fermentation is preferably conducted in a stirred tank reactor. Mixing can be supplied by an impeller, agitator or other suitable means in order to maintain the vessel contents in substantially homogeneous form.

The process of the invention can be carried out with a submerged culture of the mutant strain and under substantially oxygen deficient or anaerobic conditions. Freely mobile cells or immobilized cells can be employed.

A substrate can be added to the fermenter to multiply the yeast cells and increase biomass concentration in the fermenter. A conventional organic, fermentable carbon substrate, such as a carbohydrate can be employed for this purpose. Glucose is a preferred substrate. The organic substrate can be employed either singly or in admixture with other organic substrates.

The carbon substrate can be fed to the fermenter in aqueous solution. The concentration of the substrate in the fermentation medium will depend upon the culture conditions. In any event, the carbon substrate is employed in an amount sufficient for cell growth and cell maintenance. An aqueous solution containing about 50 g/L to about 100 g/L glucose has been found to be suitable as the carbon source.

Yeast cells for inoculation can be grown in a reaction vessel, such as a shake flask or fermenter, on a nutrient medium containing a source of assimilable carbon. A variety of culture media can be employed. A complex medium that has been found to be suitable for use in the fermentation is described in Table 3.

TABLE 3

| Complex Nutrient Medium | |
| --- | --- |
| Glucose | 100 g/l |
| Yeast Extract | 6 g/l |
| (NH$_4$)$_2$SO$_4$ | 4 g/l |

TABLE 3-continued

| Complex Nutrient Medium | |
| --- | --- |
| MgSO$_4$.7H$_2$O | 0.6 g/l |
| KH$_2$PO$_4$ | 1 g/l |

Cell growth can typically be carried out at 30° C. and pH 5.5. Biomass concentration during the growth phase in the reaction vessel can be monitored by sampling the contents of the vessel and by measuring the optical density (OD) of the sample. When the optical density is about 5 to about 35 as measured by absorbance at 660 nm, the cells should be allowed to become oxygen limited or anaerobic or both. The cells must be harvested before the glucose is depleted. Cell harvesting can be carried out with centrifugation at 4–10° C.

During the course of characterizing the mutant microorganisms, a pronounced degree of variability in PAC production was noticed. It was found that the rate and extent of PAC formation correlated with the growth phase of the culture used in the production process. In particular, the level of dissolved oxygen in the cell culture used for PAC production was found to be a primary determinant of PAC productivity. In addition, it was found that if the culture was allowed to enter stationary phase due to depletion of some nutrient other than oxygen, PAC synthesis was significantly limited. The actual density of the culture, however, does not appear to have a major bearing on the fermentation reaction. Sampling of the culture anywhere along the growth curve (early, mid, or late log phase, into stationary phase) yields similar results as long as the cells are allowed to grow anaerobically for a period of time prior to use in the PAC reaction. For example, this can be achieved by growing the microorganism in a fermenter on complex medium containing glucose (50 g/L). When biomass reaches an optical density of about 30, aeration is turned down and the media is allowed to become oxygen depleted. The cells are allowed to grow anaerobically for a period of 6 to 16 hours without allowing glucose to become depleted. To harvest, the culture can be pumped through a cooling coil submerged in ice and the cells can be removed by centrifugation.

The benzaldehyde employed in practicing the process of this invention is generally a technical or pharmaceutical grade of commercially available material. The pyruvate is usually derived from a technical or pharmaceutical grade of pyruvic acid or a non-toxic, water soluble salt thereof. A non-toxic alkali metal salt, such as sodium pyruvate is preferred.

The pyruvate and benzaldehyde can be individually added to the reaction if the reaction medium is sufficiently agitated to ensure uniform dispersion throughout the biomass. In the preferred embodiment of the invention, the pyruvate and benzaldehyde are mixed together in an aqueous medium and the resulting composition is added to the reaction.

At the start of the fermentation reaction, the concentration of benzaldehyde in the fermentation medium is generally about 5 g/L to about 20 g/L, preferably about 12 g/L to about 15 g/L. Similarly, the concentration of pyruvate in the fermentation medium at the start of the fermentation is about 5 g/L to about 20 g/L, preferably about 12 g/L to about 15 g/L.

The weight ratio of benzaldehyde to pyruvate in the fermentation medium at the start of the fermentation will generally be about 0.5:1 to about 2:1, preferably about 1:1 to about 1.2:1.

The identity of the chemical constituents in the nutrient medium and the amount of each constituent should be sufficient to meet the elemental requirements for cell mass production and should supply appropriate energy for synthesis and maintenance during PAC production.

The fermentation process can be carried out over a moderate range of temperatures. The fermentation temperature will generally be about 15° C. to about 30° C., preferably about 20° C. to about 22° C. The optimum fermentation temperature will depend upon the microorganism that is employed, and the optimum temperature can be determined with a minimum of experimentation.

The process of the invention can also be carried out over a moderate range of pH values in the culture medium. The pH will generally be about 5 to about 8, preferably about 6 to about 6.5. The pH in the culture medium may fall or rise during the fermentation. A non-toxic pH regulating agent or a buffering agent can be added to the fermentation medium as required.

The process of the invention is carried out under sufficiently sterile conditions to ensure cell viability and metabolism. This requires careful selection of the microorganism, sterilization of the apparatus used for the fermentation and possible sterilization of the reagents.

The fermenter can be operated over a range of biomass concentrations, and the optimum concentration can be determined without undue experimentation. As previously noted, biomass concentration does not appear to have a major bearing on the fermentation reaction. The practical range of values will generally depend upon process economics.

The concentration of PAC in the fermentation medium should be maximized in order to reduce the cost of product recovery. The process of this invention can be carried out at PAC concentrations of at least about 1 g/L, and preferably at PAC concentrations of at least about 10 g/L, and specifically about 12 g/L to about 15 g/L, in the fermentation medium.

The process of this invention can be carried out on a batch or a continuous basis. For the production of PAC by continuous fermentation, the microorganism can be placed in a column and a standard reaction mixture can be pumped over the column. Thiamine pyrophosphate (TPP), a cofactor for the enzyme PDCase, can be included in the standard reaction mixture, e.g. at a concentration of 0.1 mM. Fractions of column effluent can be collected and sampled quantitively for the presence of PAC.

The PAC can be recovered from the fermentation medium using conventional techniques. For example, biomass can be removed from the liquid phase in the fermentation medium by filtration, centrifugation or settling. The resulting liquid phase can be further processed to concentrate the PAC solution. PAC can be removed from the solution by solvent extraction.

PAC can be purified according to the method of Neuberg, Biochim. Z. 128:610 (1922). The GC/MS profile of the purified product shows a parent peak with a molecular weight of 150. The product of the reaction can also be determined to be the correct optical isomer, namely L-phenyl acetyl carbinol, by polarimetry. Conversion to ephedrine by reaction with methylamine has been performed and the results substantiated.

A more detailed description of procedures that can be employed to produce PAC using the mutant strains of this invention is included in commonly owned U.S. Pat. application Ser. No. 07/549,231, filed July 9, 1990, which is a continuation of 07/260,622, filed Oct. 21. 1988, now abandoned, (Attorney Docket No. SYNE-037), by Robert J. Seely, Donald L. Heefner, Robert V. Hageman, Michael J. Yarus and Sally A. Sullivan, and entitled A PROCESS FOR PRODUCING L PHENYL ACETYL CARBINOL (PAC), AN IMMOBILIZED CELL MASS FOR USE IN THE PROCESS AND A METHOD FOR PREPARING THE CELL MASS. The entire disclosure of the commonly-owned application is relied upon and incorporated by reference herein.

In summary, this invention provides an efficient process for microbial transformation of benzaldehyde to PAC and microorganisms for use in the process. Productivities of the microorganisms for PAC are high. In addition, it is possible to obtain a relatively high concentration of PAC in the fermentation liquor while reducing the formation of acetaldehyde during the transformation.

What is claimed is:

1. A method for providing a yeast organism capable of producing elevated levels of 1-phenyl acetyl carbinol (PAC) when cultured with benzaldehyde and pyruvate in an aqueous medium, wherein the method comprises,
   (A) providing a yeast organism capable of producing a measurable amount of PAC when cultured with benzaldehyde and pyruvate in an aqueous medium, wherein the organism is selected from species of *Saccharomyces cerevisiae* or from species of *Candida flareri;*
   (B) mutagenizing the organism with a chemical mutagen or by irradiation;
   (C) culturing the resulting mutated organisms in the presence of acetaldehyde under conditions to form cell colonies having reduced acetaldehyde inhibition;
   (D) isolating yeast cells from colonies having resistance to acetaldehyde inhibition; and
   (E) testing the yeast cells isolated from said colonies for yield of PAC in a fermentation with benzaldehyde and pyruvate.

2. Method as claimed in claim 1, wherein the method further comprises testing the yeast cells isolated from the colonies for yield of acetaldehyde in the fermentation with benzaldehyde and pyruvate.

3. A method for providing a microorganism capable of producing elevated levels of 1-phenyl acetyl carbinol (PAC) when cultured with benzaldehyde and pyruvate in an aqueous medium, wherein the method comprises
   (A) providing a microorganism capable of producing a measurable amount of PAC when cultured with benzaldehyde and pyruvate in an aqueous medium, wherein the organism is selected from strains of *Candida flareri:*
   (B) mutagenizing the organism with a chemical mutagen or by irradiation;
   (C) culturing the resulting mutated organisms in the presence of ephedrine under conditions to form colonies having resistance to the ephedrine inhibition;
   (D) isolating cells from colonies having resistance to ephedrine inhibition; and
   (E) testing the cells isolated from said colonies for yield of PAC in a fermentation with benzaldehyde and pyruvate.

4. Method as claimed in claim 3, wherein the method further comprises testing the cells isolated from the colonies for yield of acetaldehyde in the fermentation with benzaldehyde and pyruvate.

5. A method for providing a microorganism capable of producing elevated levels of 1-phenyl acetyl carbinol (PAC) when cultured with benzaldehyde and pyruvate in an aqueous medium, wherein the method comprises (A) providing a microorganism capable of producing a measurable amount of PAC when cultured with benzaldehyde and pyruvate in an aqueous medium, wherein the organism is selected from strains of *Candida flareri;*

(B) mutagenizing the organism with N-methyl-N'-nitro-N-nitrosoguanidine (N 76);

(C) culturing the resulting mutated organisms in the presence of PAC-dione under conditions to form colonies having resistance to PAC-dione inhibition;

(D) isolating cells from colonies having resistance to PAC-dione inhibition; and (E) testing the cells isolated from said colonies for yield of PAC in a fermentation with benzaldehyde and pyruvate.

6. Method as claimed in claim 5, wherein the method further comprises testing the cells isolated from the colonies for yield of acetaldehyde in the fermentation with benzaldehyde and pyruvate.

* * * * *